US00PP35311P3

(12) United States Plant Patent
Olesen

(10) Patent No.: US PP35,311 P3
(45) Date of Patent: Aug. 15, 2023

(54) ROSE PLANT NAMED 'POULVIC008'

(50) Latin Name: *Rosa hybrida*
Varietal Denomination: Poulvic008

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/803,631

(22) Filed: Sep. 13, 2022

(65) Prior Publication Data

US 2023/0189675 P1 Jun. 15, 2023

(30) Foreign Application Priority Data

Sep. 24, 2021 (QZ) ..... PBR 2021/2345

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./101, 116, 122
See application file for complete search history.

*Primary Examiner* — Karen M Redden

(57) ABSTRACT

A new garden rose plant of the miniature class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulvic008'.

This application claims priority to Plant Breeder's Rights Application Number 2021/2345, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulvic008', originated as a single seedling from the stated cross.

The new variety may be distinguished from its male pollen parent and female seed parent primarily by the following characteristics. The male pollen parent plant has small red flowers about 40 mm in diameter while the new variety has larger red flowers about 75 mm in diameter. The female seed parent plant has yellow flowers while the new variety has red flowers.

The objective of the hybridization of this rose variety was to create a new and distinct variety with unique qualities, such as:

1. Uniform and abundant red flowers with long lasting quality;
2. Vigorous, but compact growth when propagated on its own roots;
3. Exceptional disease resistance.

This combination of qualities is not present in previously available commercial cultivars of this type, known to the inventor, and distinguish 'Poulvic008' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulvic008' was selected in the spring of 2016 by the inventor as a single plant from the progeny of the aforementioned hybridization.

Asexual reproduction of 'Poulvic008' by rooted cuttings was first done by Mogens N. Olesen in the nursery in Fredensborg, Denmark in July, 2016. This initial and other subsequent asexual propagations conducted in controlled environments have demonstrated that the characteristics of 'Poulvic008' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulvic008'.

Specifically illustrated in FIG. 1 of the drawings are an open flower viewed from above, flower buds upon opening, flower petals detached revealing reproductive flower parts, and sepals detached revealing the characteristics of the receptacle.

DETAILED DESCRIPTION OF THE VARIETY

Figure 1:
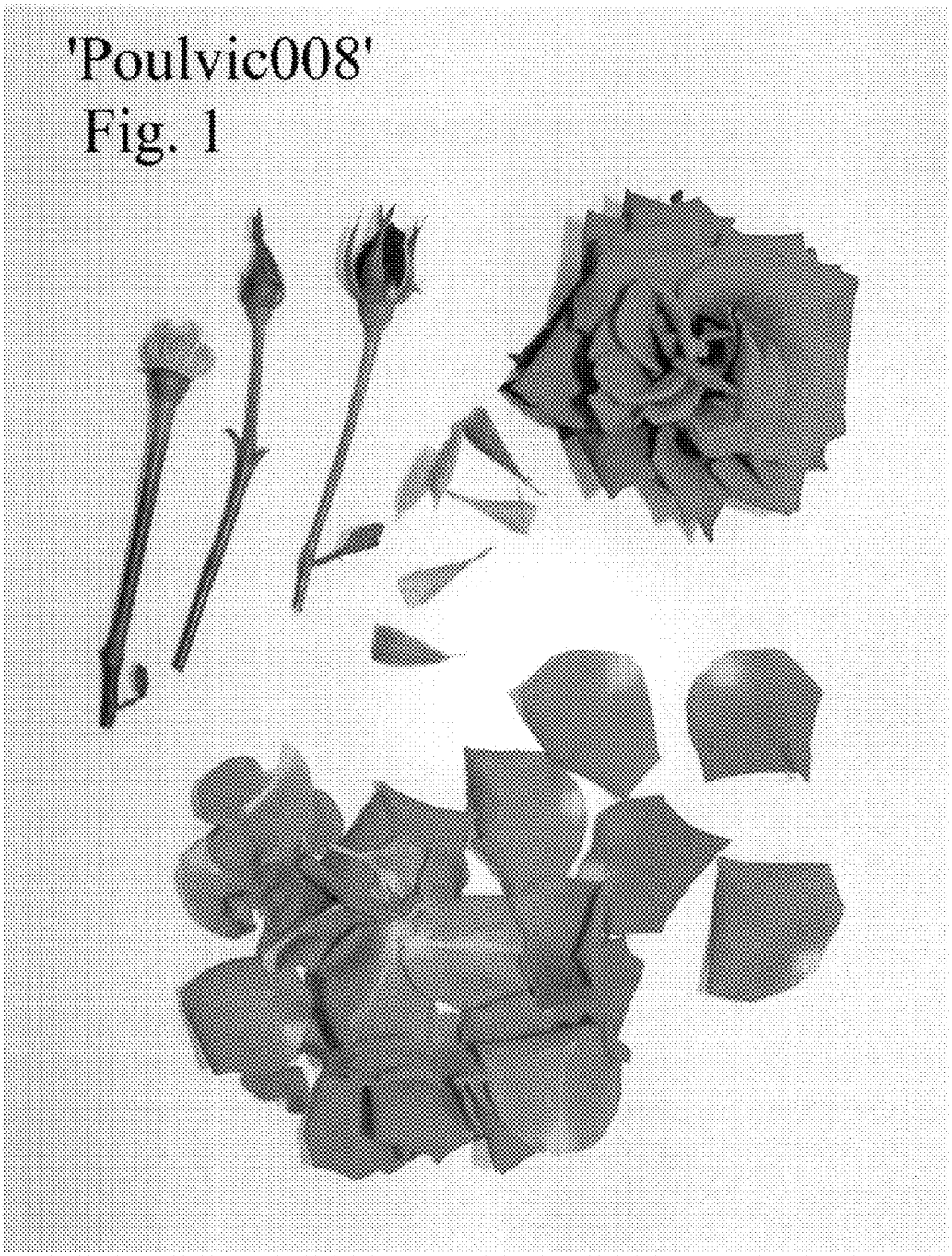
Figure 2:
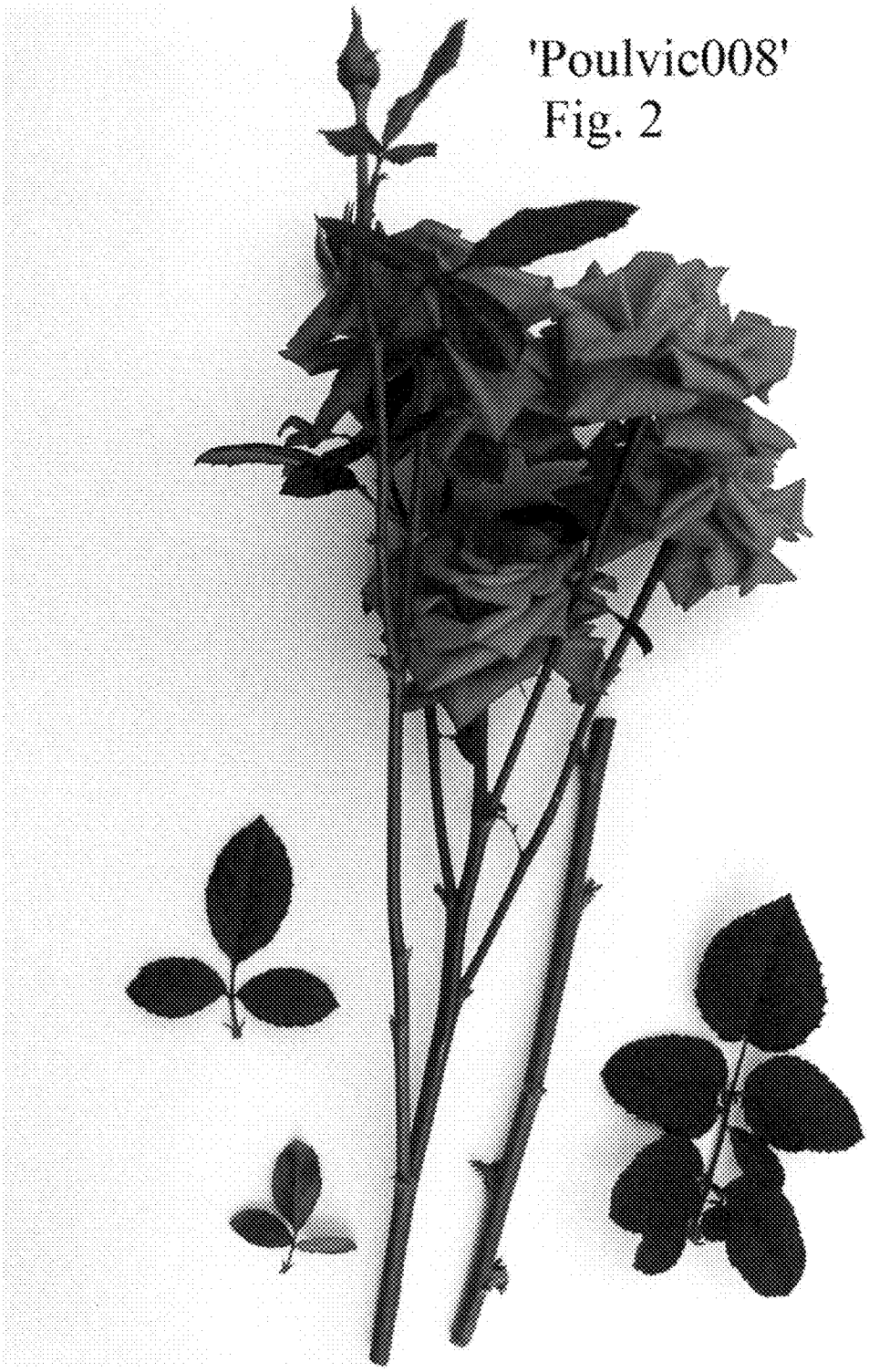
FIG. 2 illustrates bare stem, juvenile and mature leaves, and a cluster of flowers on a branch. Plants shown are 6 months of age.

The following is a description of 'Poulvic008', as observed in its growth in a glass house located in Odense Denmark. Observed plants are 6 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpar114', U.S. Plant Pat. No. 32,297 are now compared to 'Poulvic008'. The comparison variety has a flower general tonality of Red Group 46B, while the claimed plant has flower colour of Red Group 53C. While flowers of the comparison variety have 35 petals and a diameter of 65 mm, the claimed plant has a flower diameter of 75 mm with 25 flower petals.

FLOWER AND FLOWER BUD

Blooming habit: Continuous.

Flower bud:

- *Size.*—Upon opening, 24 mm in length from base of receptacle to end of bud. Bud diameter is 14 mm.
- *Bud form.*—Ovoid.
- *Bud color.*—As sepals divide petals are Greyed-Purple Group 187B.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have weak to medium foliaceous appendages on three of the five sepals.
- *Sepal size.*—30 mm long, 9 mm wide.
- *Receptacle.*—Texture: Smooth. Size: 6 mm in height, 7 mm wide. Color: Yellow-Green Group 144A. Shape: Campanulate.
- *Pedicel.*—Surface: Smooth. Length: 55 mm. Diameter: 3 mm on average. Color: Yellow-Green Group 144A. Strength: Strong.
- *Peduncle.*—Length: 50 to 150 mm. Diameter: About 4 mm. Color: Yellow-Green Group 145A. Texture: Smooth.

Flower bud development: Flower buds are borne in clusters of about 5 flower buds per stem and single.

Flower bloom:

- *Fragrance.*—None.
- *Duration.*—The blooms have a duration on the plant of approximately 28 days. Petals fall cleanly away from plant after flowers have fully matured.
- *Size.*—Flower diameter is 75 mm when open. Flower depth is 35 mm.
- *Flower shape.*—Rosette, double flower, with many slightly overlapping petals of different sizes.
- *Shape of flower, side view.*—The upper portion is convex. The lower portion is concave.

Petalage: Under normal conditions, flowers have about 25 petals.

General tonality of flower: Open flowers are Red Group 53C.

Petal color:

- *Upon opening, outer and inner petals.*—Upper surface: Red Group 53B. At the basal zone Yellow Group 5B. Lower surface: Red Group 53B with occasional streaks of Red Group 54B. The basal zone point of attachment is Yellow Group 4B.
- *After opening, outer and inner petals.*—Upper surface: Blend of Red Group 53B and Red-Purple Group N57A. Lower surface: Red-Purple Group 58B.
- *Basal petal spots, after opening.*—Upper surface: Yellow Group 5B, Lower surface: Yellow Group 4B.

Petals:

- *Petal reflex.*—Strong, bilateral.
- *Margin.*—Entire and uniform. No undulations.
- *Shape.*—Broad and elliptic. Apex shape: Rounded. Base shape: Acute.
- *Size.*—40 mm (l)×44 mm (w) on average.
- *Texture.*—Smooth.
- *Thickness.*—Average.

Petaloids:

- *Size.*—30 mm (l) by 16 mm (w).
- *Quantity.*—About 3.
- *Shape.*—Elliptical with an acute base and rounded apices.
- *Color.*—The upper side is Red Group 53B, with occasional streaks of White Group 155A and a basal petal spot of Yellow Group 5B. The lower surface is Red Group 53B and Red-Purple Group N57A blended, with streaks of Red-Purple Group 56B.

Reproductive flower parts:

- *Pollen.*—None observed.
- *Anthers.*—Size: 2 mm in length. Color: Greyed-Yellow Group 161B. Quantity: 45 on average.
- *Filaments.*—Color: Yellow Group 12A. Length: 6 mm.
- *Pistils.*—Length: 12 mm. Quantity: 35 on average.
- *Stigmas.*—Color: Greyed-Yellow Group 160C.
- *Styles.*—Color: Red Group 53C.
- *Location of stigmas.*—Superior in location relative to the length of the filaments and the height of the anthers.
- *Hips.*—None Observed.

PLANT

Plant growth: Upright. Plants are about 65 cm in height, and 48 cm wide.

Stems:

- *Color of juvenile growth.*—Yellow-Green Group 144B.
- *Color of mature growth.*—Yellow-Green Group 146A.
- *Length.*—Canes are about 35 cm from the base of the plant to the flowering portion.
- *Diameter.*—About 7 mm.
- *Internodes.*—On mature canes about 35 to 55 mm between nodes.
- *Surface texture.*—Young wood: Smooth. Older wood: Smooth.

Long prickles: None observed.

Plant foliage:

- *Compound leaf.*—142 mm (l)×110 (w).
- *Quantity.*—3 leaves per 10 cm of stem on average.
- *Leaf bearing angle to the stem.*—45 degrees.
- *Color of juvenile foliage.*—Upper side: Yellow-Green Group 147A. Lower side: Yellow-Green Group 146B with intonations of Greyed-Purple Group 183A.
- *Color of mature foliage.*—Upper side: Yellow-Green Group 147A. Lower side: Yellow-Green Group 147B.

Plant leaves and leaflets:

*Stipules*.—Size: 11 mm long, 2 mm wide. Quantity: 2 per compound leaf. Shape: Linear, slightly broad based with outward extending apices. Margins: Finely serrated. Color:.

*Petiole*.—Length: 26 mm. Diameter: 2 mm. Upper surface color: Yellow-Green Group 144A with intonations of Greyed-Purple Group 187C. Lower surface color: Yellow-Green Group 144A.

*Rachis*.—Length: 51 mm. Upper surface color: Yellow-Green Group 146A with intonations of Greyed-Purple Group 187C. Lower surface color: Yellow-Green Group 146B.

*Leaflet*.—Quantity: Normally 5 leaflets. Margins: Serrated. Size: Terminal leaflets are about 69 mm long, 44 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulvic008', substantially as illustrated and described herein, due to its abundant (color) flowers, disease resistance, and extended period of bloom.

* * * * *

'Poulvic008'

'Poulvic008'